(12) United States Patent
Mabry et al.

(10) Patent No.: US 9,012,673 B1
(45) Date of Patent: Apr. 21, 2015

(54) SYNTHESIS AND APPLICATIONS OF PERIPHERALLY ASYMMETRIC ARYL POSS COMPOUNDS

(71) Applicant: The United States of America, as represented by the Secretary of the Air Force, Washington, DC (US)

(72) Inventors: Joseph M Mabry, Lancaster, CA (US); Brian M Moore, California City, CA (US); Sean M Ramirez, Lancaster, CA (US); Gregory R Yandek, Tehachapi, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 218 days.

(21) Appl. No.: 13/624,355

(22) Filed: Sep. 21, 2012

Related U.S. Application Data

(60) Provisional application No. 61/537,125, filed on Sep. 21, 2011.

(51) Int. Cl.
*C07F 7/21* (2006.01)
*C09D 5/16* (2006.01)

(52) U.S. Cl.
CPC ............... *C07F 7/21* (2013.01); *C09D 5/1662* (2013.01)

(58) Field of Classification Search
USPC ................................. 556/460, 461
See application file for complete search history.

(56) References Cited

U.S. PATENT DOCUMENTS

| | | | |
|---|---|---|---|
| 2,687,424 A | 8/1957 | Sommer | |
| 3,382,279 A | 5/1968 | Niderprum | |
| 3,465,017 A | 9/1969 | Coutant | |
| 4,774,028 A | 9/1988 | Imai et al. | |
| 5,258,534 A | 11/1993 | Larson et al. | |
| 5,283,348 A | 2/1994 | Bank | |
| 5,629,394 A | 5/1997 | Cheradame et al. | |
| 5,912,377 A | 6/1999 | Hall et al. | |
| 6,057,402 A | 5/2000 | Zhou et al. | |
| 6,217,943 B1 | 4/2001 | Hall et al. | |
| 6,489,380 B1 | 12/2002 | Zhou et al. | |
| 6,767,930 B1 | 7/2004 | Svejda et al. | |
| 6,770,724 B1 | 8/2004 | Lichtenhan et al. | |
| 6,844,379 B2 | 1/2005 | Zhou et al. | |
| 7,053,167 B2 | 5/2006 | Ito et al. | |
| 7,291,747 B2 | 11/2007 | Oikawa et al. | |
| 7,332,822 B2 | 2/2008 | Basheer | |

(Continued)

OTHER PUBLICATIONS

Moore; Journal of Organometallic Chemistry 696 (2011) 2676-2680; published on Jul. 1, 2011.*

(Continued)

*Primary Examiner* — Sudhakar Katakam
*Assistant Examiner* — Pancham Bakshi
(74) *Attorney, Agent, or Firm* — AFMCLO/JAZ; Chastity Whitaker

(57) ABSTRACT

Asymmetric aryl polyhedral oligomeric silsesquioxanes (Ar-Poss) compounds synthesized by the "corner-capping" of phenyl$_7$Si$_7$O$_9$(OH)$_3$ with aryl trichlorosilanes are described. The ArPoss compounds have the chemical structure:

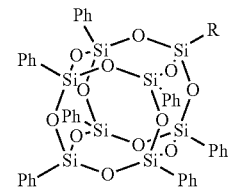

wherein Ph is

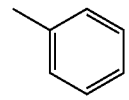

phenyl and wherein R is selected from the group consisting of:

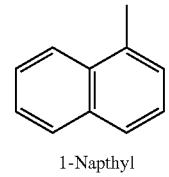 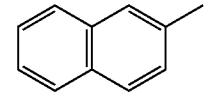

1-Napthyl  2-Naphthyl

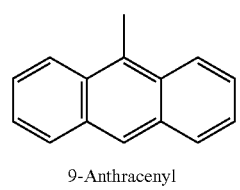 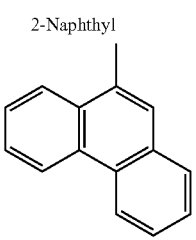

9-Anthracenyl  9-Phenanthrenyl

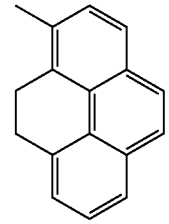

1-Pyrenyl and mixtures thereof.

6 Claims, 3 Drawing Sheets

(56) References Cited

U.S. PATENT DOCUMENTS

| | | | |
|---|---|---|---|
| 8,058,380 | B1 | 11/2011 | Vij et al. |
| 8,276,664 | B2 | 10/2012 | Gupta |
| 2001/0016616 | A1 | 8/2001 | Yeager et al. |
| 2005/0009982 | A1 | 1/2005 | Inagaki et al. |
| 2006/0194068 | A1 | 8/2006 | Katoh et al. |
| 2007/0173657 | A1 | 7/2007 | Chen et al. |
| 2008/0199805 | A1 | 8/2008 | Rushkin et al. |
| 2009/0069508 | A1 | 3/2009 | Poe et al. |
| 2010/0063244 | A1 | 3/2010 | Poe et al. |
| 2010/0068168 | A1 | 3/2010 | Song et al. |
| 2010/0098761 | A1 | 4/2010 | Song et al. |
| 2010/0159011 | A1 | 6/2010 | Lian et al. |
| 2010/0280561 | A1 | 11/2010 | Song et al. |
| 2012/0000853 | A1 | 1/2012 | Tuteja et al. |
| 2012/0015191 | A1 | 1/2012 | Treadway |
| 2012/0190532 | A1 | 7/2012 | Celiker et al. |
| 2012/0214269 | A1 | 8/2012 | Harding |

OTHER PUBLICATIONS

Moore; Abstracts of Papers, 241st ACS National Meeting &Exposition, Anaheim, CA, United States, Mar. 27-31, 2011, Poly-225. American Chemical Society: Washington, D. C.*

United States Patent Office, "Non-Final Office Action in U.S. Appl. No. 13/210,915," mailed Jun. 11, 2014, 6 pages total.

B. Seurer et al.., "Influences of POSS peripheral, architecture, and spacer group on phenylethynphthalimide reactions," Polymer Preprints, vol. 50 (2009) 820-821.

United States Patent Office, "Final Office Action in U.S. Appl. No. 13/624,151," mailed May 30, 2014, 11 pages total.

United States Patent Office, "Non-Final Office Action in U.S. Appl. No. 13/624,151," mailed Nov. 17, 2013, 12 pages total.

Alberto Fina et al., "POSS-based hybrids by melt/reactive blending," Journal of Materials Chemistry, vol. 20, (2010) pp. 9297-9305.

Brian M. Moore et al., "Asymmetric aryl polyhedral oligomeric silsequioxanes (ArPOSS) with enhanced solubility," Journal of Organometallic Chemistry, vol. 696 (2011) pp. 2676-2680.

P.D. Lickiss and F. Rataboul, Chapter 1: "Fully condensed polyhedral oligosilsesquioxanes (POSS): From synthesis to application," Adv. Organomet. Chem. vol. 57 (2008) pp. 1-116.

J. D. Lichtenhan et al., "Linear hybrid polymer building blocks: methacrylate-functionalized polyhedral oligomeric silsesquioxane monomers and polymers," Macromol. vol. 28 (1995) 8435-8437.

S.D. Rosenberg et al., "Preparation of Some Arylchlorosilanes with Arylmagnesium Chlorides" Journal Organomet. Chemistry vol. 22 (1957) pp. 1606-1607.

P. Iyer and M. R. Coleman, "Thermal and Mechanical Properties of Blended Polyimide and Amine-Functionalized Poly(orthosiloxane) Composites," Journal of Applied Polymer Science, vol. 108 (2008) pp. 2691-2699.

G. R. Yandek et al., "Effects of Peripheral Architecture on the Properties of Aryl Polyhedral Oligomeric Silsesquioxanes," J. Phys. Chem. vol. 116, (2012) pp. 16755-16765.

S. S. Chhatre et al., "Fluoroalkylated Silicon-Containing Surfaces—Estimation of Solid-Surface Energy," Appl. Mater. Interfaces. vol. 2 (2010) 3544-3554.

F. J. Feher et al., "A new route to heterosilsesquioxane frameworks," Angew. Chem., Int. Ed. vol. 37 (1998) 2663-2667.

F. J. Feher et al., "A new route to incompletely-condensed silsesquioxanes: acid-mediated cleavage and rearrangement of (c-C6H11)6Si6O9 to C2-[(c-C6H11)6Si6O8X2]," Chem. Commun. (1999) 1705-1706.

F. J. Feher et al., "A new route to incompletely-condensed silsesquioxanes: base-mediated cleavage of polyhedral oligosilsesquioxanes," Chem. Commun. (1999) 2309-2310.

F. J. Feher, "Controlled cleavage of R8Si8O12 frameworks: a revolutionary new method for manufacturing precursors to hybrid inorganic-organic materials," Chem. Commun. (1998) 399-400.

A. Tuteja et al., "Designing superoleophobic surfaces," Science. vol. 318 (2007) 1618-1622.

S. H. Phillips et al., "Developments in nanoscience: polyhedral oligomeric silsesquioxane (POSS)-polymers," Current Opinion in Solid State and Materials Science. vol. 8 (2004) 21-29.

W. Choi et al., "Fabrics with tunable oleophobicity," Adv. Mater. vol. 21 (2009) 2190-2195.

S. T. Iacono et al., "Facile synthesis of hydrophobic fluoroalkyl functionalized silsesquioxane nanostructures," Chem. Commun. (2007) 4992-4994.

J. M. Mabry et al., "Fluorinated polyhedral oliomeric silsesquioxanes (F-POSS)," Angew. Chem., Int. Ed. vol. 47 (2008) 4137-4140.

E. G. Shockey et al., "Functionalized polyhedral oligosilsesquioxane (POSS) macromers: new graftable POSS hydride, POSS α-olefin, POSS epoxy, and POSS chlorosilane macromers and POSS-siloxane triblocks," Appl. Organomet. Chem. vol. 13 (1999) 311-327.

R. Duchateau "Incompletely condensed silsesquioxanes: versatile tools in developing silica-supported olefin polymerization catalysts," Chem. Rev. vol. 102 (2002) 3525-3542.

C. Ohde et al., "Oxovandaium (IV) silsesquioxane complexes," Inorg. Chem. vol. 49 (2010) 2479-2485.

K. Pielichowski et al., "Polyhedral oligomeric silsesquioxane (POSS)-containing nanohybrid polymers," J. Adv. Polym. Sci. vol. 201 (2006) 225-296.

F. J. Feher et al., "Practical methods for synthesizing four incompletely condense silsesquioxanes from a single R8S18O12 framework," Chem. Commun. (1998) 1279-1280.

D. B. Cordes et al., "Recent developments in the chemistry of cubic polyhedral oligosilsesquioxanes," Chem. Rev. vol. 110 (2010) 2081-2173.

T. Haddad et al, "Polyhedral Oligomeric Silsequioxane (POSS)-Styrene Macromers" Organomet. vol. 11 (2001) 155-164.

A. Tuteja et al., "Robust omniphobic surfaces," PNAS. vol. 105 (2008) 18200-18205.

R. H. Baney et al., "Silsesquioxanes," Chem. Rev. vol. 95 (1995) 1409-1431.

F. J. Feher et al., "Synthesis and structural characterization of a remarkably stable, anionic, incompletely condensed silsesquioxane framework," Chem. Commun. (1997) 829-830.

H. Liu et al., "A spectroscopic investigation of incompletely condensed polyhedral oligomeric silisesquioxanes (POSS-mono-ol, POSS-diol and POSS-triol): hydrogen-bonded interaction and host-guest complex," J. Organomet. Chem. vol. 693 (2008) 1301-1308.

T. W. Dijkstra et al., "Silsesquioxane models for geminal silica surface silanol sites. A spectroscopic investigation of different types of silanols," J. Am. Chem. Soc. vol. 124 (2002) 9856-9864.

S. T. Iacono et al., "Preparation of composite fluoropolymers with enhanced dewetting using fluorinated silsesquioxanes as drop-in modifiers," J. Mater. Chem. vol. 20 (2010) 2979-2984.

F. J. Feher et al., "Facile framework cleavage reactions of a completely condensed silsesquioxane framework," J. Am. Chem. Soc. vol. 119 (1997) 11323-11324.

F. J. Feher et al., "Reactions of incompletely-condensed silsequioxanes with pentamethylantimony: a new synthesis of metallasilsesquioxanes with important implications for the chemistry of silica surfaces," J. Am. Chem. Soc. vol. 114 (1992) 3859-3866.

F. J. Feher and T. L. Tajima, "Synthesis of a molybdenum-containing silsesquioxane which rapidly catalyzes the metathesis of olefins," J. Am. Chem. Soc. vol. 116 (1994) 2145-2146.

F. J. Feher et al., "Silsesquioxanes as models for silica surfaces," J. Am. Chem. Soc. vol. 111 (1989) 1741-1748.

H. M. Cho et al., "A Mo(VI) alkylidyne complex with polyhedral oligomeric silsesquioxane ligands: homogeneous analogue of a silica-supported alkyne metathesis catalyst," J. Am. Chem. Soc. vol. 128 (2006) 14742-14743.

Michael E Wright, Chemical Modification of Fluorinated Polyimides: New Thermally Curing Hybrid Polymers with Poss, Macromolecules 2006, pp. 4710-4718.

T. S. Haddad and J. D. Lichtenhan, "Hybrid organic-inorganic thermoplastics: styryl-based polyhedral oligomeric silsesquioxane polymers," Macromol. vol. 29 (1996) 7302-7304.

K. Koh et al., "Precision synthesis of a fluorinated polyhedral oligomeric silsesquioxane-terminated polymer and surface characterization of its blend film with poly(methyl methacrylate)," Macromol. vol. 38 (2005) 1264-1270.

(56) References Cited

OTHER PUBLICATIONS

E. Lucenti et al., "Synthesis and characterization of osmium-containing silsesquioxanes: high-yield routes to {Os3(CO)10(μ-H)[μ-O)Si7O10(c-C6H11)7]} and the new clusters {Os3(CO)10(μ-H)[μ-O)Si7O9(OH)2(c-C6H11)7]}, {[Os3(CO)10(μ-H)]2[μ-O)2Si7O9(OH)(c-C6H11)7}, {Os3(CO)10(μ-H)[μ-O)Si8O11(OH)(c-C6H11)8]}, and {[Os3(CO)10(μ-H)]2(μ-O)2Si8O11(c-C6H11)}," Organomet. vol. 26 (2006) 75-82.

K. Wada et al., "Synthesis and catalytic activity of group 4 metallocene containing silsesquioxanes bearing functionalized silyl groups," Organomet. vol. 23 (2004) 5824-5832.

K. Ohno et al., "Living radical polymerization by polyhedral oligomeric silsesquioxane-holding initiators; precision synthesis of tadpole-shaped organic/inorganic hybrid polymers," Macromol. vol. 37 (2004) 8517-8522.

S. T. Iacono et al, "Synthesis, characterization, and surface morphology of pendant polyhedral oligomeric silsesquioxane perfluorocyclobutyl aryl ether copolymers," Macromol. vol. 40 (2007) 9517-9522.

Sean M. Ramirez, "Synthesis and Free Radical Polymerization of Fluorinated Polyhedral Oligomeric Silsesquioxane (F-POSS) Macromers: Precursors for Low Surface Energy Materials," Presentation to the Chemistry Department of the Air Force Academy, Colorado Springs, Colorado, Apr. 12, 2012.

R. Duchateau et al, "Silica-Grafted Diethylzinc and a Silsesquioxane-Based Zinc Alkyl Complex as Catalysts for the Alternating Oxirane-Carbon Dioxide Copolymerization," Organomet. vol. 26 (2007) 4204-4211.

Fina, A., et al., "Polyhedral Oligomeric Silsesquioxanes (POSS) Thermal Degradation," Thermochimica Acta 440, pp. 36-42 (Nov. 14, 2005).

United States Patent and Trademark Office, Non-Final Office Action in U.S. Appl. No. 14/013,600, mailed Aug. 22, 2014, 6 pages.

Braunecker et al., "Controlled/living radical polymerization: features, developments, and perspectives," Prog. Polym. Sci., vol. 32 (2007) 93-146.

Goto et al., "Mechanism and kinetics of RAFT-based living radical polymerization of styrene and methyl methacrylate," Macromol., vol. 34 (2001) 402-408.

Iacono et al., "Synthesis, characterization, and properties of chain terminated polyhedral oligomeric silsesquioxane-functionalized perfluorocycloutyl aryl ehter copolymers," Polymer., vol. 48 (2007) 4637-4645.

Mayadunne et al, "Living radical polymerization with reversible addition-fragmentation chain transfer (RAFT polymerization) using dithiocarbanatesas chain transfer agents," Macromol., vol. 32 (1999) 6977-6980.

McCormic et al., "Aqueous RAFT polymerization: recent developments in synthesis of functional water-soluble (Co)polymers with controlled structures," ACC Chem. Res., vol. 37 (2004) 312-325.

Moad et al., "Toward living radical polymerization" ACC Chem. Res., vol. 41 (2008) 1133-1142.

Thomas et al., "Kinetics and molecular weight control of the polymerization of acrylamide via RAFT" Macromol., vol. 37 (2004) 8941-8950.

Tsujii et al., "Hepta(3,3,3-trifluoropropyl) polyhedral oligomeric silsesquioxane-capped poly(n-isopropylacrylamide) telechcelics: synthesis and behavior of physical hydrogels," Macromol., vol. 34 (2001) 898-909.

Zeng et al, "Rapid deswelling and reswelling response of poly(N-isopropylacrylamide) hydrogels via formation of interpenetrating polymer networks with polyhedral oligomeric silsesquioxane-capped polyethylene oxide) amphiliphilic telechelics," J. Phys. Chem. B., vol. 3 (2009) 11831-11840.

Zeng et al, "Organic-inorganic hybrid hydrogels involving poly(N-isopropylacrylamide) and polyhedral oligomeric silsesquioxane: preparation and rapid thermoresponsive properties," J. Polym. Sci. Part B Polym. Phys., vol. 47 (2009) 504-516.

Zhang et al., "Synthesis via RAFT polymerization of tadpole-shaped organic/inorganic hyrid poly(acrylic acid) containing polyhedral oligomeric silsesquioxane (POSS) and their self-assemlby in water," Macromol., vol. 42 (2009) 2563-2569.

Isemura et al., "Dicloropentafluoroprogane as solvents for size exclusion chromatography," Chromatogr. A, vol. 1026 (2004) 109-116.

Crivello et al., "The synthesis, characterization, and photoinitiated cationic polymerization of silicon-containing epoxy resins," J. Poly. Sci. Part A: Polym. Chem., vol. 28 (1990) 479-503.

Georjon et al., "Effects of crosslink density on mechanical properties of high glass transition temperature polycyanurate networks," J. Appl. Polym. Sci., vol. 65 (1998) 2471-2479.

Guenthner et al., "A new silicon-containing bis(cyanate) ester resin with improved thermal oxidation and moisture resistance," Macromol. vol. 3 (2006) 6046-6053.

Hay et al., "6: Processing and cure schedules for cyanate ester resins," Chem & Tech Cyanate Ester Resins (1994) 22 pages total.

Marella et al., "An investigation on the hydrolysis of polyphenolic cyanate esters using near-IR spectroscopy," Drexel University Thesis, (2008) 102 pages total.

Maya et al., "Oligodimethylsiloxane linked cyanate ester resins," Macromol., vol. 35 (2009) 460-466.

Shimp et al., "Moisture effects and their control in the curing of polycyanate resins," ACS PMSE Prepr., vol. 66 (1992) 504-505.

Shimp et al., "Cyanate esters—a new family of high temperature thermosetting resins," High Temp. Polym. (1989) 127-140.

Wright, "The synthesis of new silane based bis(cyanate) ester monomers for use in high performance composite resins," Polym. Preprint., vol. 45 (2004) 2 pages total.

Yameen et al., "Polycyanurate thermoset networks with high thermal, mechanical, and hydrolytic stability based on liquid multifunctional cyanate ester monomers with bisphenol A and AF units," Macromol. Chem. Phys., vol. 209 (2008) 1673-1685.

Mconnell, "Resins for the hot zone, part I: polyimides," Composites World (2009) 6 pages total.

Mconnell, "Resins for the hot zone, part II: BMIs, CEs, benzoxazines and phthalonitriles," Composites World (2009) 6 pages total.

United States Patent and Trademark Office, Non-Final Office Action in U.S. Application No. 113/748,730, mailed Jul. 22, 2014, 8 pages.

Cheng et al., "Phosphonium-containing ABA triblock copolymers: controlled free radical polymerization of phosphonium ionic liquids," Macromol., vol. 44 (2011) 6509-6517.

Destarac, "On the critical role of RAFT agent design in reversible addition-fragmentation chain transfer (RAFT) polymerization," Poly. Rev., vol. 51 (2011) 163-187.

Lu et al., "L-proline functionalized polymers prepared by RAFT polymerization and their assemblies as supported organicatalysts," Macromol., vol. 44 (2011) 7233-7241.

Rameriz et al., "Incompletely condensed fluoroalkyl silsesquioxanes and derivatives: precursors for low surface energy materials," JACS, vol. 133 (2011) 20084-20087.

Stamenovic et al., "Norbornenyl-bsed RAFT agents for the preparation of functional polymers via thiol-ene chemistry," Macromol., vol. 44 (2011) 5619-5630.

Tan et al., "Tailoring micelle formation and gelation in (PEG-P(MA-POSS)) amphiphilic hybrid block copolymers," Macrmol., vol. 44 (2011) 622-631.

Wang et al., "Hepta(3,3,3-trifluoropropyl) polyhedral oligomeric silsesquioxane-capped poly(N-isopropylacrylamide) telechelics: synthesis and behavior of physical hydrogels," ACS Appl. Mater. Interfaces, vol. 3 (2011) 898-909.

Zeng et al., "Nanostructures and surface hydrophobicity of epoxy thermosets containing hepta(3,3,3-trifluoropropyl) polyhedral oligomeric silsesquioxane-capped polyhedral oligomeric silsesquioxane-capped poly(hydroxyehter of bisphenol A) telechelics." J. Colloid Interf Sci., vol. 363 (2011) 250-260.

Guenthner et al., "Synthesis, cure kinetics, and physical properties of a new tricyanate ester with enhanced molecular flexibility" with Supplementary Content, Polymer, vol. 52 (2011) 3933-3942, 30 pages total.

Guenthner et al., "Cure characteristics of tricyanate ester high-temperature composite resins," For presentation at a SAMPE conference to be held in Long Beach, CA, May 24, 2011, 22 pages total.

United States Patent and Trademark Office, Final Office Action in U.S. Appl. No. 14/013,600, mailed Dec. 4, 2014, 5 pages total.

\* cited by examiner wherein Ph is:

phenyl and R is:

1-Napthyl   2-Naphthyl   9-Anthracenyl   9-Phenanthrenyl   1-Pyrenyl and mixtures thereof.

SYNTHESIS AND APPLICATIONS OF PERIPHERALLY ASYMMETRIC ARYL POSS COMPOUNDS

CROSS REFERENCE TO RELATED APPLICATION

This application claims the benefit of and priority to the filing date of U.S. provisional application Ser. No. 61/537,125, filed Sep. 21, 2011, incorporated herein by reference in its entirety.

RIGHTS OF THE GOVERNMENT

The invention described herein may be manufactured and used by or for the Government of the United States for all governmental purposes without the payment of any royalty thereon.

FIELD OF THE INVENTION

This invention relates to synthesis methods and applications for the production and use of organic/inorganic hybrid polyhedral oligomeric silsesquioxane (POSS) nanomaterials.

BACKGROUND OF THE INVENTION

The synthesis of hybrid organic-inorganic materials that combine the diversity and ease of processing of organic polymers with the thermo-chemical stability and oxidative resistance of ceramics remains a goal of material researchers worldwide. Polyhedral Oligomeric SilSesquioxanes (POSS) have emerged as effective multi-functional, highly tailorable additives, capable of improving polymer performance. Each of these nanoparticles features an inorganic $SiO_{1.5}$ core, as well as an organic corona, which helps to determine overall solubility. Compounds based on this architectural framework have received a great deal of attention as nearly ideal hybrid materials due to the synergy of the silsesquioxane cage and organic character at the molecular level.

In contrast to most other forms of nanoscale reinforcement, POSS compounds have been shown to improve processing characteristics when either blended into polymer hosts or incorporated by copolymerization. Although both techniques have distinct advantages, inert blending is generally the preferred method, offering facile modification of commercial polymers without the necessity for polymer synthesis and balancing stoichiometry. Furthermore, blending techniques generally provide access to a greater material design space in the context of nanoparticle assembly. However, the availability of thermally stable, inert POSS additives for the purpose of reinforcing high temperature polymers by this method is limited. Further development would be of benefit to a range of potential products requiring lightweight materials for energy efficiency, aerospace, and durable infrastructure applications.

Aryl-functionalized silsesquioxanes, such as $phenyl_8Si_8O12$ ($Ph_8Si_8O_{12}$), have been in existence for decades, appearing well suited for the preparation of high-performance, aromatic nanocomposites. However, the high symmetry and low dipole moments of $Ph_8Si_8O_{12}$ promote highly-efficient crystalline packing. This is manifested in poor solubility in organic solvents, and a neutral response to mechanical shear, thus severely limiting incorporation into polymers.

To circumvent these limitations, several research groups have focused on the modification of aryl-functionalized POSS compounds. For example, $vinyl_8Si_8O_{12}$ was functionalized with aromatic photo-luminescent compounds via Heck coupling. (Para-iodophenyl)$_8Si_8O_{12}$ was synthesized as a platform for coupling additional organic moieties to POSS cages. Other work attached $Ph_8Si_8O_{12}$ to polybenzimidazole via an in-situ Friedel-Crafts acylation copolymerization reaction. Researchers have found that copolymerized $Ph_8Si_8O_{12}$ was more thoroughly dispersed in the polymer host than physically blended $Ph_8Si_8O_{12}$.

Unfortunately, none of the above methods have proven to be fully successful in overcoming the limitations of non-reactive, aryl-functionalized POSS compounds such as poor solubility in organic solvents, and a neutral response to mechanical shear. There remains a need for aryl-functionalized POSS compounds which overcome these limitations.

SUMMARY OF THE INVENTION

Applicants have discovered peripherally asymmetric aryl polyhedral oligomeric silsesquioxane (ArPOSS) compounds, synthesized by "corner-capping" methodology, which overcome the limitations of $Ph_8Si_8O_{12}$ through geometric consideration of the POSS cage periphery. Synthesis of these compounds proceeds through a-capping reaction with uncondensed phenyl POSS alcohols using trichlorosilanes with terminal aryl groups that are geometrically larger in size than phenyl groups, such as naphthalene, anthracene, penanthrene, and pyrene. These corner-capped POSS compounds demonstrate enhanced solubility in organic solvents and aromatic polymers, enabling a more facile route to the fabrication of high temperature nanocomposites, without conciliating absolute peripheral aromaticity thus retaining superior thermal stability.

DETAILED DESCRIPTION OF THE INVENTION

Figure 1:
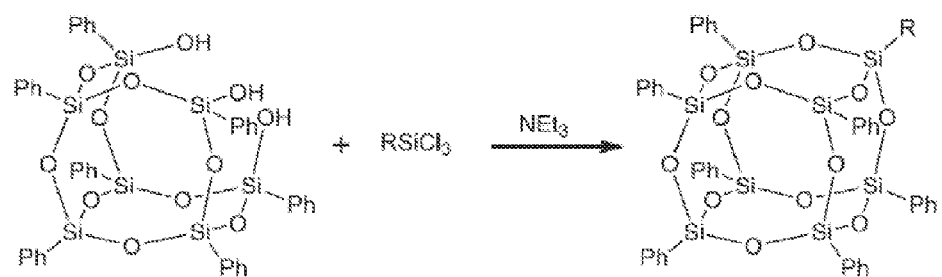
FIG. 1 shows the synthesis of corner-capped POSS cages.
Figure 1:
Figure 1:
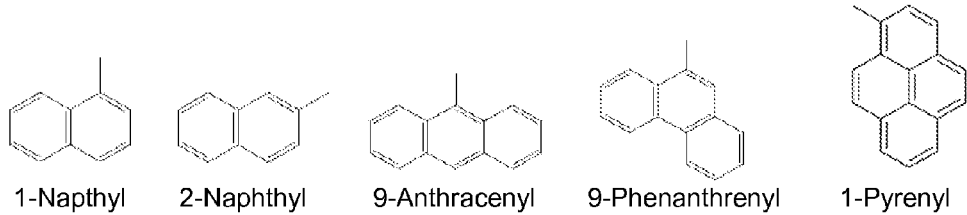

This invention describes Aromatic POSS structures synthesized by the "corner capping" of $phenyl_7Si_7O_9(OH)_3$ with aryl trichlorosilanes. The desired aryl trichlorosilanes were synthesized by reaction of an aryl Grignard or lithium reagent with SiCl4 under reaction conditions similar to those previously reported. See, e.g., S. D. Rosenberg, J. J. Walburn, H. E. Ramdsden, *Journal Organomet. Chem.* 22 (1957) pages 1606-1607, incorporated herein by reference. The aryl trichlorosilanes ($ArSiCl_3$) (Ar=1-naphthlyl, 2-naphthyl, 9-Anthracethrenyl, 9-phenanthrenyl, and 1-pyrenyl) were coupled with $phenyl_7Si_7O_9(OH)_3$ under basic conditions to yield the desired, well-defined (Aryl)$phenyl_7Si_8O_{12}$ structures shown in FIG. 1.

The resulting peripherally asymmetric aryl polyhedral oligomeric silsesquioxane (ArPOSS) compound have the chemical structure:

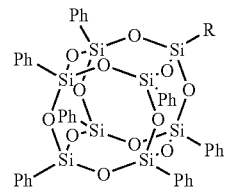

wherein Ph is

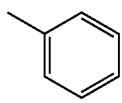

phenyl and wherein R is selected from the group consisting of

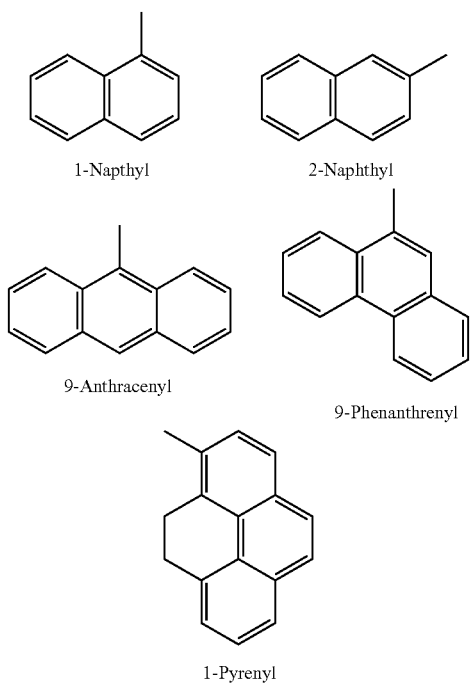

and mixtures thereof.

The preferred compounds include: (1-Naphthyl)phenyl$_7$Si$_8$O$_{12}$, (2-Naphthyl)phenyl$_7$Si$_8$O$_{12}$, (9-Anthracethrenyl)phenyl$_7$Si$_8$O$_{12}$, (9-Phenanthrenyl)phenyl$_7$Si$_8$O$_{12}$ and (1-Pyrenyl)phenyl$_7$Si$_8$O$_{12}$.

Figure 2:
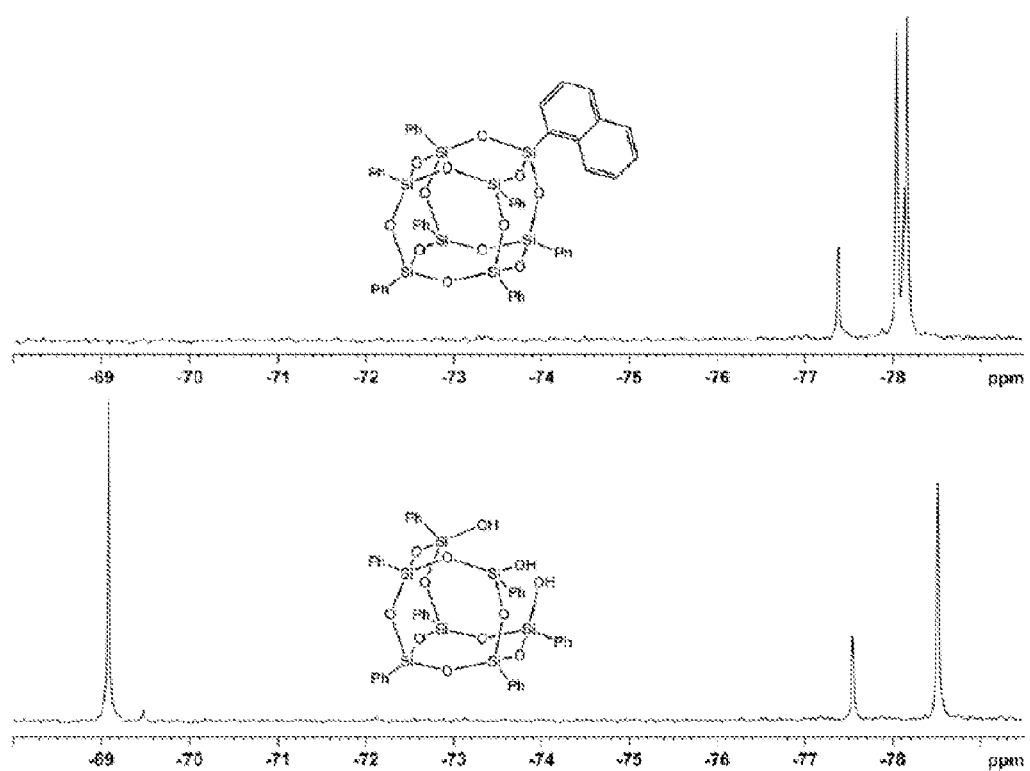
FIG. 2 compares the NMR spectrum of symmetric $phenyl_8Si_8O_{12}$ with peripherally asymmetric (1-naphthyl) $phenyl_7Si_8O_{12}$.

The desired products of these reactions were separated from by-products and starting materials via filtration and methanol washings. Previous work has proven this synthetic strategy as an effective technique for coupling trichlorosilanes to silanols. See, e.g., J. D. Lichtenhan, Y. A. Otonari, M. J. Carr, *Macromolecules* 29 (1995) pages 8435-8437, incorporated herein by reference. These POSS cage structures were confirmed on the basis of multinuclear NMR ($^1$H, $^{13}$C and $^{29}$Si) and elemental combustion analysis (CHN). The absence of silanol NMR peaks was used to confirm reaction completion. The initial chemical shifts of the $^{29}$Si NMR peaks for phenyl$_7$Si$_7$O$_9$(OH)$_3$ are –69.08, –77.54, and –78.51 ppm, respectively, in a ratio of 3:1:3. For comparison, the chemical shift of the single peak for symmetric phenyl$_8$Si$_8$O$_{12}$ is –78.07 ppm. When the corner-capping reaction is complete on the asymmetric compounds, the $^{29}$Si NMR peaks are shifted with respect to the additional substituent aryl group. For example, the peaks of (1-naphthyl)phenyl$_7$Si$_8$O$_{12}$ are shifted to 77.37, –78.05, –78.14, and –78.17 ppm, respectively, in a ratio of 1:3:1:3, as seen in FIG. 2. Similar peak shifts in $^{29}$Si NMR spectra were observed for the remaining corner-capped compounds, though the order of peak integration is occasionally different.

The influence of the prescribed peripheral asymmetry of these compounds on solubility was determined by visual measurements in five organic solvents, including chloroform (CHCl$_3$), tetrahydrofuran (THF), phenyl ether (PE), toluene (Tol), and dimethyl formamide (DMF), summarized in Table 1.

The poor solubility of symmetric phenyl$_8$Si$_8$O$_{12}$ (2) has been previously documented exhibiting only limited solubility (~1 mg/mL) in CHCl$_3$ and thus, serving as the benchmark for this work. The substitution of a single polycyclic aromatic ring on the POSS cage improves solubility substantially in most cases. However, it is difficult to predict the influence of each aromatic group on the observed solubility, as well as in which solvent the solubility will be affected. Modification with a 1-naphthyl group to produce (1-naphthyl)phenyl$_7$Si$_8$O$_{12}$ (3) results in solubility in CHCl$_3$ and THF exceeding 100 mg/mL and the observance of more finite solubility in the other investigated solvents. Modification with a 2-naphthyl group to produce (2-naphthyl)phenyl$_7$Si$_8$O$_{12}$ (4) increases solubility in PE and DMF, but reduces solubility in THF and CHCl$_3$, when compared to (1-naphthyl)phenyl$_7$Si$_8$O$_{12}$ (3). Substitution with a phenanthrenyl group to produce (9-phenanthrenyl)phenyl$_7$Si$_8$O$_{12}$ (5) results in comparable solubility in THF to that of phenyl$_8$Si$_8$O$_{12}$ (2), as well as the highest solubility in DMF and toluene of any compound examined. Limited solubility gains in comparison with the other polycyclic aromatic groups are observed with pyrenyl substitution, with (1-pyrenyl)phenyl$_7$Si$_8$O$_{12}$ (6) exhibiting the lowest solubility of the four corner-capped POSS cages in the examined solvents, albeit a noteworthy improvement over that of phenyl$_8$Si$_8$O$_{12}$ (2).

TABLE 1

Solubility (mg/ml) of aromatic POSS compounds in organic solvents

| # | CHCl$_3$ | THF | PE | Tol | DMF |
|---|---|---|---|---|---|
| 2 | 1 | a | a | a | a |
| 3 | 104 | 120 | 15 | a | 24 |
| 4 | 55 | 28 | 53 | a | 35 |
| 5 | 52 | 117 | 25 | 27 | 57 |
| 6 | 7 | 10 | 4 | 5 | 5 |

$^a$ Insoluble

Figure 3:
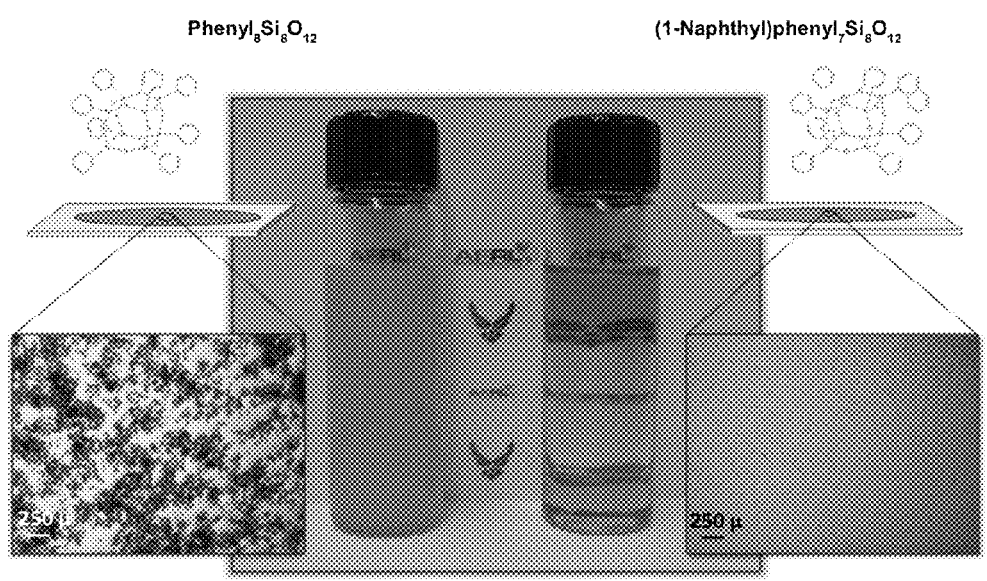
FIG. 3 compares photographs of PEI solutions containing symmetric $phenyl_8Si_8O_{12}$ with peripherally asymmetric (1-naphthyl)$phenyl_7Si_8O_{12}$ and optical micrographs of drop cast films from the two PEI solutions.

To examine the phase behavior of this new class of peripherally asymmetric POSS nanoparticles with a representative aromatic polymer, attempts were made to solubilize both phenyl$_8$Si$_8$O$_{12}$ and (1-naphthyl)phenyl$_7$Si$_8$O$_{12}$ in polyetherimide (Ultem 1000, PEI). Chloroform solutions were prepared at a solute concentration of 5 weight percent PEI and POSS concentration of 5 weight percent with respect to PEI. Subsequent films from these solutions were drop cast onto glass substrates, dried under vacuum, and annealed at 220° C., above the glass transition temperature of PEI, to promote equilibrium phase formation. In accordance with the solubility study, the solution containing asymmetric (1-naphthyl)phenyl$_7$Si$_8$O$_{12}$ is transparent, indicating superior solubility in chloroform, in contrast to that containing symmetric phenyl$_8$Si$_8$O$_{12}$, which is cloudy, as shown in FIG. 3.

Qualitatively, the dried and annealed films were visually observed to be of contrasting appearance. The film containing symmetric phenyl$_8$Si$_8$O$_{12}$ was significantly more opaque, indicating a greater degree of phase separation. Examination of the films by microscopy revealed aggregated particles of phenyl$_8$Si$_8$O$_{12}$ at length scales greater than 1 mm in some regions of the PEI host. Phase separation in the film containing (1-naphthyl)phenyl$_7$Si$_8$O$_{12}$ appears to be limited to less than 5 microns in the post-annealed state, revealing improved solubility in the predominately aromatic polymer, shown in FIG. 3.

Replacing a single phenyl ring on phenyl$_8$Si$_8$O$_{12}$ with one of several polycyclic aromatic groups results in compounds that exhibit improved solubility in organic solvents and aromatic polymers, without significant sacrifices in thermal stability. These improvements, relative to the state-of-the-art materials, are realized through a disruption of symmetry and reduced ordering in the forms of crystallization and/or aggregation. These compounds offer new opportunities to blend ArPOSS with a variety of organic/polymer materials, a possibility that was previously impractical due to the insolubility of phenyl$_8$Si$_8$O$_{12}$.

Applications for this new class of ArPOSS compounds include, but are not limited to: the mechanical and thermal reinforcement of organic and preceramic polymers, protective coatings for organic substrates, and surfactants for the hybridization of organic and inorganic materials.

The following examples are examples of reduction to practice of the present invention and confirmation that the principles described in the present invention are therefore valid but should not be construed as in any way limiting the scope of the invention.

EXAMPLES

Materials

Phenyl$_7$Si$_7$O$_9$(OH)$_3$ was obtained from Hybrid Plastics, while additional silicon-containing organic compounds were purchased from Gelest. Remaining chemicals were purchased from Aldrich. All chemicals were used without further purification unless otherwise noted. All reactions were performed under an atmosphere of dry nitrogen. Flasks were oven-dried and allowed to cool under nitrogen prior to use.

Characterization $^1$H, $^{13}$C, and $^{29}$Si NMR spectra were obtained on Bruker 300-MHz and 400-MHz spectrometers using 5 mm o.d. tubes. Sample concentrations were approx. 10% (w/v) in chloroform-d. Combustion analysis was performed by Atlantic Microlab, Inc. Norcross, Ga. Thermogravimetric analysis (TGA) was performed on a TA Instruments 5000 using 5-10 mg of material, at a scan rate of 10° C./min under a nitrogen atmosphere.

General Synthesis of Chlorosilane Compounds

1-Naphthyltrichlorosilane

Under a dry nitrogen atmosphere, a solution of 1-bromonaphthalene (27.7 g, 0.134 mol) in THF (175 mL) was added slowly to a suspension of magnesium turnings (3.9 g, 0.16 mol) in THF (15 mL) that had previously been activated with an iodine crystal. After cooling to room temperature, this Grignard reagent was added via canula to a THF (70 mL) solution of SiCl$_4$ (25.1 g, 0.148 mol) and stirred overnight. The mixture was evaporated to dryness, extracted with hexane and filtered to remove Mg halide. The product was distilled at 120° C. under dynamic vacuum to give a 67% yield (23.6 g, 0.0902 mol) of product. $^1$H NMR (CDCl$_3$, ppm) 8.46 (dd, 1H), 8.21 (dd, J=6.8 Hz, J=1.2 Hz, 1H), 8.09 (d, J=8.4 Hz, 1H), 7.96 (d, J=7.6 Hz, 1H), 7.69 (t, 1H), 7.62 (t, 1H), 7.57 (t, 1H). 13C{$^1$H}NMR (CDCl$_3$, ppm) 135.51 (CH), 134.42 (C), 134.07 (CH), 133.58 (C), 129.37 (CH), 127.91 (C), 127.45 (CH), 127.16 (CH), 126.56 (CH), and 124.65 (CH). $^{29}$Si{$^1$H} (CDCl3, ppm) –0.17 (s).

2-Naphthyltrichlorosilane

Yield 31%. $^1$H NMR (CDCl$_3$, ppm) 8.40 (s, 1H), 7.96 (d, 2H), 7.89 (d, 1H), 7.82 (dd, J=8.4 Hz, J=1.5 Hz, 1H), 7.62 (m, 2H). $^{13}$C{$^1$H}NMR (CDCl3, ppm) 135.49 (CH), 135.06 (C), 132.28 (C), 128.90 (CH), 128.54 (C), 128.52 (CH), 128.34 (CH), 127.85 (CH), 127.34 (CH), and 127.02 (CH). $^{29}$Si{$^1$H} (CDCl$_3$, ppm) –0.87 (s).

9-Phenanthrenyltrichlorosilane

Yield 58%. $^1$H NMR (CDCl$_3$, ppm) 8.76 (m, 1H), 8.68 (d, J=8.4 Hz, 1H), 8.48 (s, 1H), 8.43 (m, 1H), 7.99 (dd, J=7.9 Hz, J=0.5 Hz, 1H), 7.75 (m, 3H), 7.67 (t, 1H). $^{13}$C{$^1$H} NMR (CDCl$_3$, ppm) 139.02 (CH), 132.30 (C), 131.36 (C), 130.48 (C), 130.10 (CH), 129.77 (C), 129.45 (CH), 128.18 (CH), 127.25 (CH), 127.19 (CH), 127.14 (CH), 126.77 (C), 123.49 (CH), and 122.56 (CH). $^{29}$Si{$^1$H} (CDCl$_3$, ppm) –0.51 (s).

1-Pyrenyltrichlorosilane

Under a dry nitrogen atmosphere, n-BuLi (10.6 mL, 1.6 M) in hexanes was added drop-wise to a cooled (–60° C.) solution of 1-bromopyrene (5.01 g, 0.018 mol) in THF/Et$_2$O (1:1) (80 mL) and stirred for 2 hours at –60° C. The solution was cooled to –90° C. and a THF solution of SiCl$_4$ (8.66 g, 0.051 mol) (10 mL) was added slowly and stirred for 24 hours at room temperature. The reaction mixture was evaporated to dryness, washed in Et$_2$O (100 mL), and filtered to remove any unreacted 1-bromopyrene and LiBr. The filtrate was collected and evaporated to dryness to give a 48% yield of 1-trichlorosilylpyrene, a yellow powder. $^1$HNMR (CDCl$_3$, ppm) 8.66 (d, J=9.3 Hz, 1H), 8.59 (d, J=8.1 Hz, 1H), 8.30 (m, 5H), 8.11 (m, 2H). $^{13}$C{$^1$H} NMR (CDCl$_3$, ppm) 136.18 (C), 135.85 (C), 133.13 (CH), 132.06 (C), 131.30 (C), 131.22 (CH), 130.31 (CH), 127.96 (CH), 127.67 (CH), 127.61 (CH), 126.65 (CH), 125.61 (C), 125.01 (CH), and 124.39 (C). 29Si{1H} (CDCl$_3$, ppm) –1.64 (s).

General Synthesis of POSS Compounds

1-Naphthyl)phenyl$_7$Si$_8$O$_{12}$ (1-NapPh$_7$Si$_8$O$_{12}$)

Under a dry nitrogen atmosphere, phenyl$_7$Si$_7$O$_9$(OH)$_3$ (19.0 g, 0.0211 mol) was dissolved in THF (150 mL). A solution of 1-naphthyltrichlorosilane (5.63 g, 0.0215 mol) in THF (50 mL) was then slowly added. A dilute solution of triethylamine (6.84 g, 0.0676 mol) in THF (100 mL) was then added over a 90 min period under vigorous stirring. The reaction was allowed to proceed overnight. The solution was then filtered and the volume reduced under dynamic vacuum. The product was dissolved in ether and an aqueous wash (4:1) was performed to remove water-soluble byproducts. The solution was again reduced under vacuum and the remaining oil was dissolved in THF. The solution was precipitated in methanol and then filtered to obtain a 92% yield of product (21.0 g, 0.0194 mol). $^1$H NMR (CDCl$_3$, ppm) 8.51 (m, 1H-nap), 8.04 (dd, J=6.8 Hz, J=1.3 Hz, 1H-nap), 7.98 (d, J=8.3 Hz, 1H-nap), 7.81 (m, 15H-nap/ph), 7.39 (m, 24H-nap/ph). $^{13}$C{$^1$H} NMR (CDCl$_3$, ppm) 136.45 (C-nap), 135.36 (CH-nap), 134.22, 134.21, 134.18 (3:1:3, CH-ph), 133.16 (C-nap), 131.51 (CH-nap), 130.83, 130.80, 130.77 (3:1:3, CH-ph), 130.17, 130.13, 130.03 (3:1:3, C-ph), 128.65 (CH-nap), 128.34 (CH-nap), 128.23 (C-nap), 127.91, 127.88, 127.85 (3:1:3, CHph), 126.50 (CH-nap), 125.73 (CH-nap), and 124.83 (CH-nap). $^{29}$Si{$^1$H} (CDCl$_3$, ppm) –77.37, –78.05, –78.14, and –78.17 (1:3:1:3). Combustion Anal. (Calcd): C, 57.68 (57.64); H, 3.81 (3.91).

(2-Naphthyl)phenyl$_7$Si$_8$O$_{12}$ (2-NapPh$_7$Si$_8$O$_{12}$)

Yield 90%. $^1$H NMR (CDCl$_3$, ppm) 8.31 (s, 1H-nap), 7.84 (m, 18H nap/ph), 7.45 (m, 23H-nap/ph). $^{13}$C{$^1$H} NMR (CDCl$_3$, ppm) 135.91 (CH-nap), 134.51 (C-nap), 134.22

(CH-ph), 132.59 (C-nap), 130.82, 130.80 (3:4, CH-ph), 130.14 (C-ph), 129.58 (CH-nap), 128.46 (CHnap), 127.89 (CH-ph), 127.71 (CH-nap), 127.47 (C-nap), 127.29 (CHnap), 127.06 (CH-nap), and 126.03 (CH-nap). $^{29}$Si{$^1$H} (CDCl$_3$, ppm) −77.94, −78.14, and −78.18 (1:3:4). Combustion Anal. Calcd: C, 57.28 (57.64); H, 3.87 (3.91).

(9-Phenanthrenyl) phenyl$_7$Si8O$_{12}$ (PhenPh$_7$Si$_8$O$_{12}$)

Yield 79%. $^1$H NMR (CDCl$_3$, ppm) 8.74 (d, J=7.6 Hz, 1H-phen), 8.68 (d, J=8.3 Hz, 1H-phen), 8.51 (dd, J ¼ 7.8 Hz, J ¼ 1.2 Hz, 1 Hphen), 8.31 (s, 1H-phen), 7.84 (m, 15H-phen/ph), 7.64 (m, 4H-phen), 7.43 (m, 21H-ph). 13C{1H} NMR (CDCl$_3$, ppm) 138.35 (CH-phen), 134.24, 134.23 (3:4, CH-ph), 133.89 (C-phen), 131.66 (C-phen), 130.83 (CH-ph), 130.59 (C-phen), 130.18, 130.14, 130.03 (3:1:3, C-ph), 129.97 (C-phen), 129.21 (CH-phen), 127.91, 127.88 (3:4, CHph), 127.11 (C-phen), 126.86 (CH-phen), 126.60 (CH-phen), 126.43 (CH-phen), 122.92 (CH-phen), and 122.40 (CH-phen). $^{29}$Si{$^1$H} (CDCl$_3$, ppm) −77.28, −78.06, −78.12, and −78.18 (1:3:3:1). Combustion Anal. (Calcd): C, 59.10 (59.33); H, 3.84 (3.91).

(1-Pyrenyl)phenyl$_7$Si$_8$O$_{12}$ (PyPh$_7$Si$_8$O$_{12}$)

Yield 29%. $^1$H NMR (CDCl3, ppm) 8.72 (d, J=9.2 Hz, 1H-py), 8.43 (d, J=7.6 Hz, 1H-py), 8.21 (m, 2H-py), 8.12 (m, 3H-py), 8.04 (m, 2H-py), 7.80 (m, 14H-ph), 7.37 (m, 21H-ph). $^{13}$C{$^1$H} NMR (CDCl$_3$, ppm) 136.09 (py-C), 134.29, 134.24 (3:4, CH-ph), 133.34 (py-C), 133.30 (py-CH), 131.14 (py-C), 130.87, 130.81 (4:3, CH-ph), 130.74 (py-C), 130.24, 130.20, 130.10 (3:1:3, C-ph), 128.66 (py-CH), 128.11 (py-CH), 127.95, 127.91 (3:4, CH-ph), 127.78 (py-CH), 127.47 (py-CH), 125.91 (py-CH), 125.59 (py-CH), 125.42 (py-CH), 125.27 (py-C), 124.60 (py-C), 124.50 (py-C), and 124.04 (py-CH). $^{29}$Si{$^1$H} (CDCl$_3$, ppm) −76.80, −77.82, and −77.93 (1:3:4). Combustion Anal. (Calcd): C, 59.77 (60.18); H, 3.75 (3.83).

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A peripherally asymmetric aryl polyhedral oligomeric silsesquioxane (ArPOSS) compound having the chemical structure:

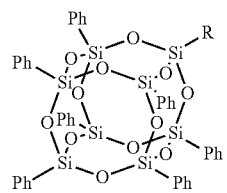

wherein Ph is phenyl; and
wherein R is selected from the group consisting of naphthyl, anthracenyl, phenanthrenyl, and pyrenyl.

2. The peripherally asymmetric ArPOSS compound of claim 1, wherein R is

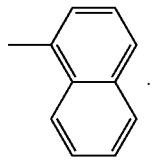

3. The peripherally asymmetric ArPOSS compound of claim 1, wherein R is

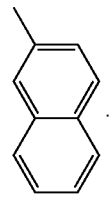

4. The peripherally asymmetric ArPOSS compound of claim 1, wherein R is

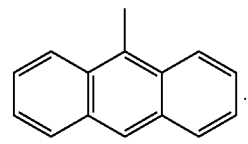

5. The peripherally asymmetric ArPOSS compound of claim 1, wherein R is

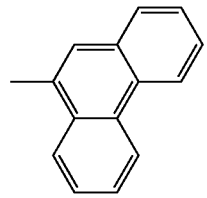

6. The peripherally asymmetric ArPOSS compound of claim 1, wherein R is

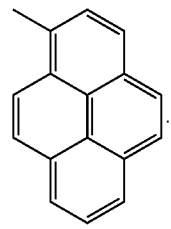 [SMILES: Cc1ccc2ccc3cccc4ccc1c2c34]

* * * * *